(12) United States Patent
Stulen

(10) Patent No.: US 8,709,031 B2
(45) Date of Patent: Apr. 29, 2014

(54) METHODS FOR DRIVING AN ULTRASONIC SURGICAL INSTRUMENT WITH MODULATOR

(75) Inventor: Foster B. Stulen, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/595,880

(22) Filed: Aug. 27, 2012

(65) Prior Publication Data
US 2012/0323265 A1 Dec. 20, 2012

Related U.S. Application Data

(62) Division of application No. 11/888,081, filed on Jul. 31, 2007, now Pat. No. 8,252,012.

(51) Int. Cl.
*A61B 17/32* (2006.01)

(52) U.S. Cl.
USPC .......................................... 606/169

(58) Field of Classification Search
USPC ........... 433/86, 102, 103, 118, 119, 141–144, 433/166; 604/22; 606/157, 159, 167, 169, 606/170, 180
See application file for complete search history.

(56) References Cited

U.S. PATENT DOCUMENTS

| | | |
|---|---|---|
| 969,528 A | 9/1910 | Disbrow |
| 1,570,025 A | 1/1926 | Young |
| 2,704,333 A | 3/1955 | Calosi et al. |
| 2,736,960 A | 3/1956 | Armstrong |
| 2,849,788 A | 9/1958 | Creek |
| RE25,033 E | 8/1961 | Balamuth et al. |
| 3,015,961 A | 1/1962 | Roney |
| 3,513,848 A | 5/1970 | Winston et al. |
| 3,526,219 A | 9/1970 | Balamuth |
| 3,614,484 A | 10/1971 | Shoh |
| 3,636,943 A | 1/1972 | Balamuth |
| 3,776,238 A | 12/1973 | Peyman et al. |
| 3,805,787 A | 4/1974 | Banko |
| 3,830,098 A | 8/1974 | Antonevich |
| 3,854,737 A | 12/1974 | Gilliam, Sr. |
| 3,862,630 A | 1/1975 | Balamuth |
| 3,900,823 A | 8/1975 | Sokal et al. |

(Continued)

FOREIGN PATENT DOCUMENTS

| | | |
|---|---|---|
| CN | 1634601 A | 7/2005 |
| CN | 1640365 A | 7/2005 |

(Continued)

OTHER PUBLICATIONS

International Search Report for PCT/US2008/071701, Dec. 18, 2008 (9 pages).

(Continued)

*Primary Examiner* — Ashley Fishback

(57) ABSTRACT

Methods for driving a surgical instrument are disclosed. The surgical instrument includes a transducer configured to produce vibrations along a longitudinal axis at a predetermined frequency. An end effector is adapted to couple to the transducer and extends along the longitudinal axis. The end effector includes a body having a proximal end and a distal end. The distal end is movable relative to the longitudinal axis by the vibrations produced by the transducer. A drive module is coupled to the transducer to generate a modulated drive signal. The distal end of the end effector is movable in response to the vibrations produced by the transducer in response to the modulated drive signal.

6 Claims, 10 Drawing Sheets

(56) References Cited

U.S. PATENT DOCUMENTS

| | | |
|---|---|---|
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 4,156,187 A | 5/1979 | Murry et al. |
| 4,188,927 A | 2/1980 | Harris |
| 4,200,106 A | 4/1980 | Douvas et al. |
| 4,306,570 A | 12/1981 | Matthews |
| 4,445,063 A | 4/1984 | Smith |
| 4,491,132 A | 1/1985 | Aikins |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,649,919 A | 3/1987 | Thimsen et al. |
| 4,708,127 A | 11/1987 | Abdelghani |
| 4,712,722 A | 12/1987 | Hood et al. |
| 4,827,911 A | 5/1989 | Broadwin et al. |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,903,696 A | 2/1990 | Stasz et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,026,387 A | 6/1991 | Thomas |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| 5,162,044 A | 11/1992 | Gahn et al. |
| 5,163,537 A | 11/1992 | Radev |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,213,569 A | 5/1993 | Davis |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,275,609 A | 1/1994 | Pingleton et al. |
| 5,282,800 A | 2/1994 | Foshee et al. |
| 5,304,115 A | 4/1994 | Pflueger et al. |
| D347,474 S | 5/1994 | Olson |
| 5,322,055 A | 6/1994 | Davison et al. |
| 5,324,299 A | 6/1994 | Davison et al. |
| 5,344,420 A | 9/1994 | Hilal et al. |
| 5,346,502 A | 9/1994 | Estabrook et al. |
| 5,353,474 A | 10/1994 | Good et al. |
| 5,357,423 A | 10/1994 | Weaver et al. |
| 5,366,466 A | 11/1994 | Christian et al. |
| 5,371,429 A | 12/1994 | Manna |
| D354,564 S | 1/1995 | Medema |
| 5,381,067 A | 1/1995 | Greenstein et al. |
| 5,403,312 A | 4/1995 | Yates et al. |
| 5,411,481 A | 5/1995 | Allen et al. |
| 5,419,761 A | 5/1995 | Narayanan et al. |
| 5,421,829 A | 6/1995 | Olichney et al. |
| 5,438,997 A | 8/1995 | Sieben et al. |
| 5,449,370 A | 9/1995 | Vaitekunas |
| 5,471,988 A | 12/1995 | Fujio et al. |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,562,609 A | 10/1996 | Brumbach |
| 5,562,610 A | 10/1996 | Brumbach |
| 5,601,601 A | 2/1997 | Tal et al. |
| 5,603,773 A | 2/1997 | Campbell |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,730,752 A | 3/1998 | Alden et al. |
| 5,733,074 A | 3/1998 | Stöck et al. |
| 5,741,226 A | 4/1998 | Strukel et al. |
| 5,792,135 A | 8/1998 | Madhani et al. |
| 5,810,859 A | 9/1998 | DiMatteo et al. |
| 5,817,084 A | 10/1998 | Jensen |
| 5,827,323 A | 10/1998 | Klieman et al. |
| 5,828,160 A | 10/1998 | Sugishita |
| 5,836,897 A | 11/1998 | Sakurai et al. |
| 5,843,109 A | 12/1998 | Mehta et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,906,628 A | 5/1999 | Miyawaki et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,980,510 A | 11/1999 | Tsonton et al. |
| 5,989,274 A | 11/1999 | Davison et al. |
| 5,989,275 A | 11/1999 | Estabrook et al. |
| 5,993,972 A | 11/1999 | Reich et al. |
| 6,024,741 A | 2/2000 | Williamson, IV et al. |
| 6,033,375 A | 3/2000 | Brumbach |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,110,127 A | 8/2000 | Suzuki |
| 6,113,594 A | 9/2000 | Savage |
| 6,129,735 A | 10/2000 | Okada et al. |
| 6,132,368 A | 10/2000 | Cooper |
| 6,139,320 A | 10/2000 | Hahn |
| 6,139,561 A | 10/2000 | Shibata et al. |
| 6,142,615 A | 11/2000 | Qiu et al. |
| 6,152,902 A | 11/2000 | Christian et al. |
| 6,159,160 A | 12/2000 | Hsei et al. |
| 6,159,175 A | 12/2000 | Strukel et al. |
| 6,165,150 A | 12/2000 | Banko |
| 6,204,592 B1 | 3/2001 | Hur |
| 6,206,844 B1 | 3/2001 | Reichel et al. |
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |

(56) References Cited

U.S. PATENT DOCUMENTS

| | | |
|---|---|---|
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,340,352 B1 | 1/2002 | Okada et al. |
| 6,352,532 B1 | 3/2002 | Kramer et al. |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,610,059 B1 | 8/2003 | West, Jr. |
| 6,616,450 B2 | 9/2003 | Mossle et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,676,660 B2 | 1/2004 | Wampler et al. |
| 6,678,621 B2 | 1/2004 | Stulen et al. |
| 6,679,899 B2 | 1/2004 | Wiener et al. |
| 6,682,544 B2 | 1/2004 | Mastri et al. |
| 6,689,146 B1 | 2/2004 | Himes |
| 6,716,215 B1 | 4/2004 | David et al. |
| 6,731,047 B2 | 5/2004 | Kauf et al. |
| 6,733,506 B1 | 5/2004 | McDevitt et al. |
| 6,762,535 B2 | 7/2004 | Take et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,783,524 B2 | 8/2004 | Anderson et al. |
| 6,786,382 B1 | 9/2004 | Hoffman |
| 6,786,383 B2 | 9/2004 | Stegelmann |
| 6,790,216 B1 | 9/2004 | Ishikawa |
| 6,802,843 B2 | 10/2004 | Truckai et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,923,804 B2 | 8/2005 | Eggers et al. |
| 6,926,716 B2 | 8/2005 | Baker et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,677 B2 | 9/2005 | Nita et al. |
| 6,945,981 B2 | 9/2005 | Donofrio et al. |
| D511,145 S | 11/2005 | Donofrio et al. |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 7,001,335 B2 | 2/2006 | Adachi et al. |
| 7,011,657 B2 | 3/2006 | Truckai et al. |
| 7,033,357 B2 | 4/2006 | Baxter et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,378 B2 | 9/2006 | Salameh et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,204,820 B2 | 4/2007 | Akahoshi |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,285,895 B2 | 10/2007 | Beaupré |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,331,410 B2 | 2/2008 | Yong et al. |
| 7,353,068 B2 | 4/2008 | Tanaka et al. |
| 7,354,440 B2 | 4/2008 | Truckai et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |

(56) References Cited

U.S. PATENT DOCUMENTS

| | | |
|---|---|---|
| 7,408,288 B2 | 8/2008 | Hara |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,494,468 B2 | 2/2009 | Rabiner et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,534,243 B1 | 5/2009 | Chin et al. |
| D594,983 S | 6/2009 | Price et al. |
| 7,549,564 B2 | 6/2009 | Boudreaux |
| 7,559,450 B2 | 7/2009 | Wales et al. |
| 7,567,012 B2 | 7/2009 | Namikawa |
| 7,578,820 B2 | 8/2009 | Moore et al. |
| 7,654,431 B2 | 2/2010 | Hueil et al. |
| 7,665,647 B2 | 2/2010 | Shelton, IV et al. |
| 7,670,334 B2 | 3/2010 | Hueil et al. |
| 7,674,263 B2 | 3/2010 | Ryan |
| 7,691,098 B2 | 4/2010 | Wallace et al. |
| 7,713,202 B2 | 5/2010 | Boukhny et al. |
| 7,714,481 B2 | 5/2010 | Sakai |
| D618,797 S | 6/2010 | Price et al. |
| 7,751,115 B2 | 7/2010 | Song |
| 7,770,774 B2 | 8/2010 | Mastri et al. |
| 7,770,775 B2 | 8/2010 | Shelton, IV et al. |
| 7,780,054 B2 | 8/2010 | Wales |
| 7,780,659 B2 | 8/2010 | Okada et al. |
| 7,784,662 B2 | 8/2010 | Wales et al. |
| 7,798,386 B2 | 9/2010 | Schall et al. |
| 7,806,891 B2 | 10/2010 | Nowlin et al. |
| 7,810,693 B2 | 10/2010 | Broehl et al. |
| 7,824,401 B2 | 11/2010 | Manzo et al. |
| 7,837,699 B2 | 11/2010 | Yamada et al. |
| 7,854,735 B2 | 12/2010 | Houser et al. |
| D631,155 S | 1/2011 | Peine et al. |
| 7,861,906 B2 | 1/2011 | Doll et al. |
| 7,876,030 B2 | 1/2011 | Taki et al. |
| D631,965 S | 2/2011 | Price et al. |
| 7,892,606 B2 | 2/2011 | Thies et al. |
| 7,901,423 B2 | 3/2011 | Stulen et al. |
| 7,905,881 B2 | 3/2011 | Masuda et al. |
| 7,922,651 B2 | 4/2011 | Yamada et al. |
| 7,959,050 B2 | 6/2011 | Smith et al. |
| 7,959,626 B2 | 6/2011 | Hong et al. |
| 7,976,544 B2 | 7/2011 | McClurken et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,089,197 B2 | 1/2012 | Rinner et al. |
| 8,142,461 B2 | 3/2012 | Houser et al. |
| 8,152,825 B2 | 4/2012 | Madan et al. |
| 8,157,145 B2 | 4/2012 | Shelton, IV et al. |
| 8,162,966 B2 | 4/2012 | Connor et al. |
| 8,177,800 B2 | 5/2012 | Spitz et al. |
| 8,182,502 B2 | 5/2012 | Stulen et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,226,675 B2 | 7/2012 | Houser et al. |
| 8,236,019 B2 | 8/2012 | Houser |
| 8,252,012 B2 | 8/2012 | Stulen |
| 8,253,303 B2 | 8/2012 | Giordano et al. |
| 8,257,377 B2 | 9/2012 | Wiener et al. |
| 8,319,400 B2 | 11/2012 | Houser et al. |
| 8,323,302 B2 | 12/2012 | Robertson et al. |
| 8,334,635 B2 | 12/2012 | Voegele et al. |
| 8,344,596 B2 | 1/2013 | Nield et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0052617 A1 | 5/2002 | Anis et al. |
| 2002/0077550 A1 | 6/2002 | Rabiner et al. |
| 2002/0156493 A1 | 10/2002 | Houser et al. |
| 2003/0036705 A1 | 2/2003 | Hare et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0199193 A1 | 10/2004 | Hayashi et al. |
| 2004/0204728 A1 | 10/2004 | Haefner |
| 2004/0260300 A1 | 12/2004 | Gorensek et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0079878 A1 | 4/2006 | Houser |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206115 A1 | 9/2006 | Schomer et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0239028 A1 | 10/2007 | Houser et al. |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |

(56) References Cited

U.S. PATENT DOCUMENTS

| | | |
|---|---|---|
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234709 A1 | 9/2008 | Houser |
| 2008/0234710 A1 | 9/2008 | Neurohr et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0149801 A1 | 6/2009 | Crandall et al. |
| 2009/0270853 A1 | 10/2009 | Yachi et al. |
| 2009/0270899 A1 | 10/2009 | Carusillo et al. |
| 2009/0318945 A1 | 12/2009 | Yoshimine et al. |
| 2009/0327715 A1 | 12/2009 | Smith et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0193567 A1 | 8/2010 | Scheib et al. |
| 2010/0268211 A1 | 10/2010 | Manwaring et al. |
| 2010/0298743 A1 | 11/2010 | Nield et al. |
| 2010/0298851 A1 | 11/2010 | Nield |
| 2010/0331870 A1 | 12/2010 | Wan et al. |
| 2011/0009850 A1 | 1/2011 | Main et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0196286 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0288452 A1 | 11/2011 | Houser et al. |
| 2012/0029546 A1 | 2/2012 | Robertson |
| 2012/0059289 A1 | 3/2012 | Nield et al. |
| 2012/0078139 A1 | 3/2012 | Aldridge et al. |
| 2012/0078247 A1 | 3/2012 | Worrell et al. |
| 2012/0083783 A1 | 4/2012 | Davison et al. |
| 2012/0083784 A1 | 4/2012 | Davison et al. |
| 2012/0184946 A1 | 7/2012 | Price et al. |
| 2012/0203257 A1 | 8/2012 | Stulen et al. |
| 2012/0259353 A1 | 10/2012 | Houser et al. |
| 2012/0265196 A1 | 10/2012 | Turner et al. |
| 2012/0269676 A1 | 10/2012 | Houser et al. |
| 2012/0289984 A1 | 11/2012 | Houser et al. |
| 2012/0310262 A1 | 12/2012 | Messerly et al. |
| 2012/0310263 A1 | 12/2012 | Messerly et al. |
| 2012/0310264 A1 | 12/2012 | Messerly et al. |

FOREIGN PATENT DOCUMENTS

| | | |
|---|---|---|
| CN | 1694649 A | 11/2005 |
| CN | 1922563 A | 2/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1433425 B1 | 6/2006 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| EP | 2298154 A2 | 3/2011 |
| GB | 2032221 A | 4/1980 |
| GB | 2379878 B | 11/2004 |
| GB | 2447767 B | 8/2011 |
| JP | 4-30508 U | 3/1992 |
| JP | 6-104503 A | 4/1994 |
| JP | 09-503146 A | 3/1997 |
| JP | 2002-263579 A | 9/2002 |
| JP | 2003-310627 A | 5/2003 |
| JP | 2005027026 A | 1/2005 |
| JP | 2005-066316 A | 3/2005 |
| JP | 2006-158525 A | 6/2006 |
| JP | 2006217716 A | 8/2006 |
| WO | WO 92/22259 A2 | 12/1992 |
| WO | WO 93/14708 A1 | 8/1993 |
| WO | WO 95/09572 A1 | 4/1995 |
| WO | WO 98/37815 A1 | 9/1998 |
| WO | WO 01/54590 A1 | 8/2001 |
| WO | WO 01/95810 A2 | 12/2001 |
| WO | WO 2004/037095 A2 | 5/2004 |
| WO | WO 2005/122917 A1 | 12/2005 |
| WO | WO 2006/042210 A2 | 4/2006 |
| WO | WO 2006/058223 A2 | 6/2006 |
| WO | WO 2006/129465 A1 | 12/2006 |
| WO | WO 2007/008710 A2 | 1/2007 |
| WO | WO 2007/047531 A2 | 4/2007 |
| WO | WO 2007/143665 A2 | 12/2007 |
| WO | WO 2008/016886 A2 | 2/2008 |
| WO | WO 2008/130793 A1 | 10/2008 |
| WO | WO 2009/018406 A2 | 2/2009 |

(56) References Cited

FOREIGN PATENT DOCUMENTS

WO     WO 2009/027065 A1     3/2009
WO     WO 2011/144911 A1     11/2011

OTHER PUBLICATIONS

Australian Patent Examination Report No. 1, Application No. 2008296695, dated Nov. 23, 2012 (4 pages).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the Internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 29/404,676, filed Oct. 24, 2011.
U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601 filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.

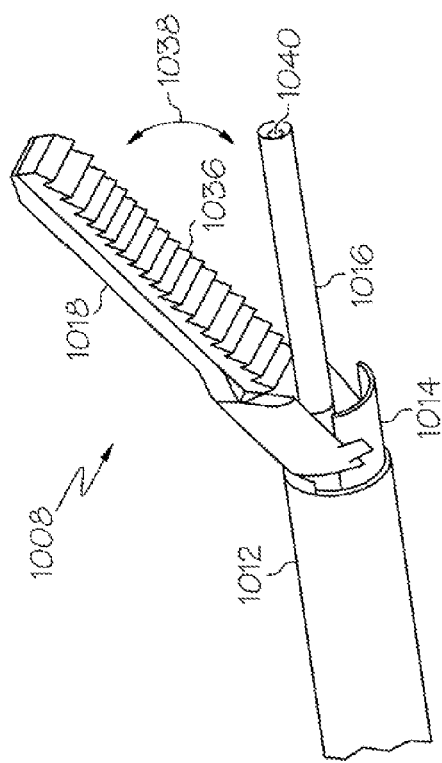
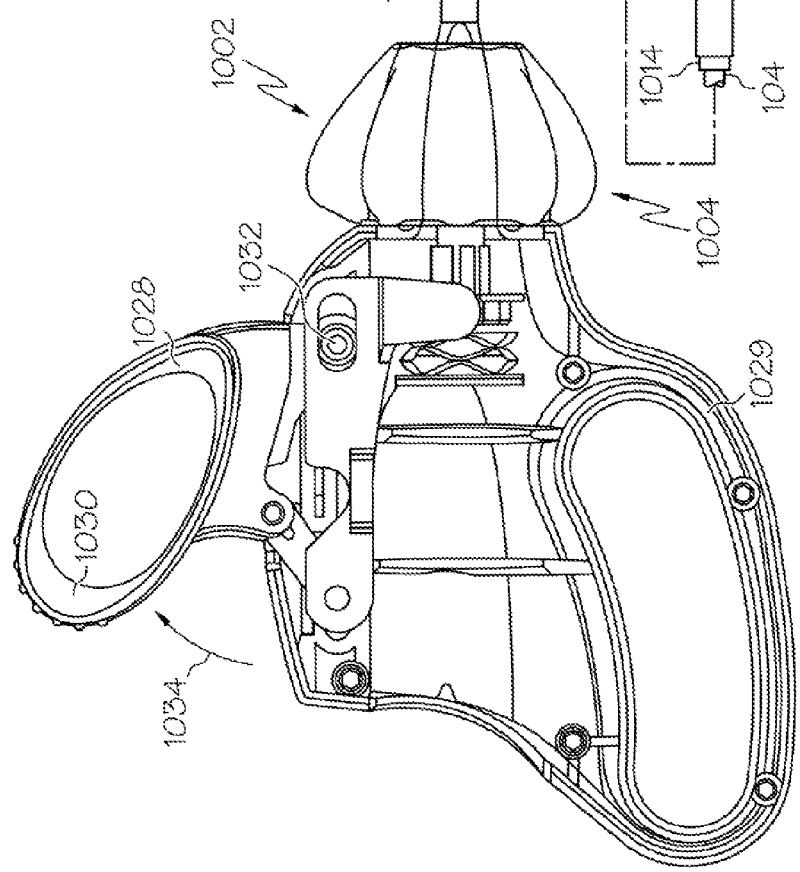
FIG. 3C
FIG. 3B

METHODS FOR DRIVING AN ULTRASONIC SURGICAL INSTRUMENT WITH MODULATOR

CROSS REFERENCE TO RELATED APPLICATION

The present application is a divisional application claiming priority under 35 U.S.C. §121 from co-pending U.S. patent application Ser. No. 11/888,081, entitled ULTRASONIC SURGICAL INSTRUMENT WITH MODULATOR, filed on Jul. 31, 2007, now U.S. Pat. No. 8,252,012, the entire disclosure of which is incorporated by reference herein.

BACKGROUND

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate tissue using energy in the form of mechanical vibrations transmitted to a surgical end effector at ultrasonic frequencies. Ultrasonic vibrations transmitted to organic tissue at suitable energy levels with a suitable end effector may be used to cut, dissect, elevate, or coagulate tissue or separate muscle tissue from bone cut. Solid core technology ultrasonic instruments are particularly advantageous because of the amount of ultrasonic energy that may be transmitted from the ultrasonic transducer to the surgical end effector through an ultrasonic transmission waveguide. Such instruments may be used for open procedures or minimally invasive procedures, such as endoscopic or laparoscopic procedures, wherein the end effector is passed through a trocar to reach the surgical site.

Activating or exciting the end effector of such instruments at ultrasonic frequencies induces longitudinal vibratory movement that generates localized heat within adjacent tissue, facilitating both cutting and coagulating. Because of the nature of ultrasonic instruments, a particular ultrasonically actuated end effector may be designed to perform numerous functions, including, for example, cutting, clamping, and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. When an end effector is attached to a transducer the overall system frequency may be the same frequency as the transducer itself.

The transducer and the end effector may be designed to resonate at two different frequencies and when joined or coupled may resonate at a third frequency. The zero-to-peak amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.

The longitudinal excursion is defined as the peak-to-peak (p-t-p) amplitude, which is just twice the amplitude of the sine wave or 2 A.

Solid core ultrasonic surgical instruments may be divided into two types, single element end effector devices and multiple-element end effectors. Single element end effector devices include instruments such as scalpels (e.g., blades, sharp hook blades, dissecting hook blades, curved blades) and ball coagulators. Single-element end effector instruments have limited ability to apply blade-to-tissue pressure when the tissue is soft and loosely supported. Substantial pressure may be necessary to effectively couple ultrasonic energy to the tissue. The inability of a single-element end effector to grasp the tissue results in a further inability to fully coapt tissue surfaces while applying ultrasonic energy, leading to less-than-desired hemostasis and tissue joining. The use of multiple-element end effectors such as clamping coagulators includes a mechanism to press tissue against an ultrasonic blade that can overcome these deficiencies.

Ultrasonic clamp coagulators provide an improved ultrasonic surgical instrument for cutting/coagulating tissue, particularly loose and unsupported tissue, wherein the ultrasonic blade is employed in conjunction with a clamp for applying a compressive or biasing force to the tissue, to achieve faster coagulation and cutting of the tissue with less attenuation of the blade motion.

As the distal end of the end effector, or more particularly, the blade, cuts through or coagulates tissue it comes into contact with fluid. The fluid may comprise irrigation fluid, blood, tissue particles and/or any combination thereof. When the distal end of an ultrasonically actuated end effector contacts the fluid, a fine mist in the form of a diverging plume of fluid particles may emanate from the distal end of the end effector. This plume of mist is generally undesirable because it may impair the visibility of the surgical site. It would be desirable to provide an ultrasonic instrument with a reduced mist plume emanating from the distal end of the end effector when it is activated with energy at ultrasonic frequencies.

SUMMARY

In one embodiment, a method is provided to drive transducer of a surgical instrument, where the transducer is configured to produce vibrations along a longitudinal axis at a predetermined frequency. An end effector is adapted to couple to the transducer and extends along the longitudinal axis. The end effector comprises a body having a proximal end and a distal end. The distal end is movable relative to the longitudinal axis by the vibrations produced by the transducer. A drive module is coupled to the transducer to generate a modulated drive signal. The distal end of the end effector is movable in response to the vibrations produced by the transducer in response to the modulated drive signal.

FIGURES

The novel features of the various embodiments are set forth with particularity in the appended claims. The various embodiments, however, both as to organization and methods of operation, may best be understood by reference to the following description, taken in conjunction with the accompanying drawings as follows.

FIG. 3B illustrates one embodiment of a clamp coagulator comprising a multi-element end effector as shown in FIG. 1B.

FIG. 3C illustrates a perspective view of the multi-element end effector as shown in FIGS. 1B and 3B.

DESCRIPTION

Figure 1A:
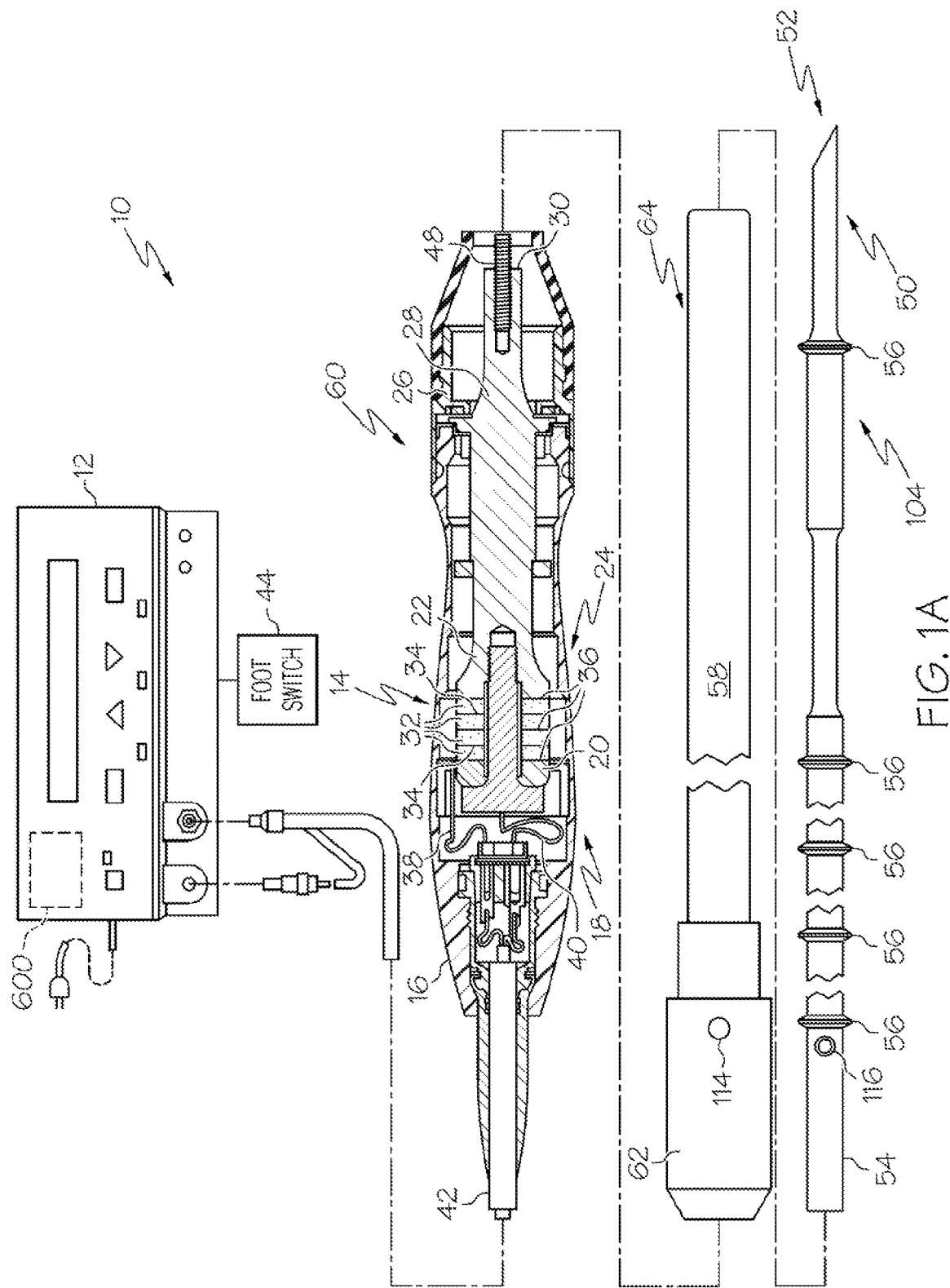
FIG. 1A illustrates one embodiment of an ultrasonic system comprising a single element end effector.

Before explaining the various embodiments in detail, it should be noted that the embodiments are not limited in its application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and blade configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

In one general aspect, the various embodiments are directed to a surgical instrument with a modulator circuit to reduce mist at a distal end of an ultrasonic end effector. The surgical instrument may comprise a transducer configured to produce vibrations along a longitudinal axis at a predetermined frequency. An ultrasonic blade extends along the longitudinal axis and is coupled to the transducer. The ultrasonic blade comprises a body having a proximal end and a distal end. The distal end is movable relative to the longitudinal axis by the vibrations produced by the transducer. The body comprises a treatment region that extends from the proximal end to the distal end. The body includes a neck portion protruding from the proximal end adapted to couple to the transducer. A modulator circuit generates a drive signal to mitigate or reduce mist.

The various embodiments relate, in general, to ultrasonic generator and/or modulator circuits to control the mist plume emanating from an ultrasonically actuated end effector. In one embodiment, the ultrasonic generator and/or modulator circuit generate modulated drive signals that reduce the mist plume emanating from the distal end of an ultrasonically actuated end effector such as a blade. The modulated drive signals reduce the mist plume and improve the visibility at the surgical site during surgery. A modulator circuit may be configured to modulate the amplitude of the drive signal (e.g., current or voltage), the frequency of the drive signal, or any combination thereof. The modulated drive signal applied to the end effector controls the radiation pressure experienced by a fluid droplet particle contacting the distal end of the end effector. The modulated drive signal drives the various mist droplets at different distances from the distal end of the end effector at different relative rates. The difference in relative motion between the mist droplets provides greater opportunities for them to collide and results in the mist droplets coalescing or globulizing. Once the mist droplets coalesce or globalize to a certain size, gravitational force will cause the larger mist droplets to drop out of the mist plume. Thus reducing the size of the mist plume and improving visibility at the surgical site.

Examples of ultrasonic surgical instruments are disclosed in U.S. Pat. Nos. 5,322,055 and 5,954,736 and in combination with ultrasonic blades and surgical instruments disclosed in U.S. Pat. Nos. 6,309,400 B2, 6,278,218 B1, 6,283,981 B1, and 6,325,811 B1, for example, are incorporated herein by reference in their entirety. These references disclose ultrasonic surgical instrument and blade configurations where a longitudinal mode of the blade is excited. Because of asymmetry or asymmetries, these blades may exhibit transverse and/or torsional motion where the characteristic "wavelength" of this non-longitudinal motion is generally less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e., will have at least longitudinal motion along the length extending from its distal end, an antinode of longitudinal motion, to the first nodal position of longitudinal motion that is proximal to the tissue effector portion).

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments is defined solely by the claims. The features illustrated or described in connection with one exemplary embodiment may be combined with the features of other embodiments. Such modifications and variations are intended to be included within the scope of the claims.

FIG. 1A illustrates one embodiment of an ultrasonic system 10 comprising a single element end effector. One embodiment of the ultrasonic system 10 comprises an ultrasonic signal generator 12 coupled to an ultrasonic transducer 14, a hand piece assembly 60 comprising a hand piece housing 16, and an ultrasonically actuatable single element end effector or ultrasonically actuatable blade 50. The ultrasonic transducer 14, which is known as a "Langevin stack", generally includes a transduction portion 18, a first resonator portion or end-bell 20, and a second resonator portion or fore-bell 22, and ancillary components. The total construction forms a resonator. The length of the ultrasonic transducer 14 is preferably an integral number of one-half wavelengths ($n\lambda/2$; where "n" is any positive integer; e.g., n=1, 2, 3 . . . ) as will be described herein. An acoustic assembly 24 includes the ultrasonic transducer 14, a nose cone 26, a velocity transformer 28, and a surface 30.

It will be appreciated that the terms "proximal" and "distal" are used herein with reference to a clinician gripping the hand piece assembly 60. Thus, the blade 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the amplitude of the ultrasonic vibration as the velocity transformer 28, or alternately may have no amplification. A suitable vibrational frequency range may be about 20 Hz to 120 kHz and a well-suited vibrational frequency range may be about 30-100 kHz. One example operational vibrational frequency may be approximately 55.5 kHz.

Piezoelectric elements 32 may be fabricated from any suitable material, such as, for example, lead zirconate-titanate, lead meta-niobate, lead titanate, barium titanate, or other piezoelectric ceramic materials. Each of positive electrodes 34, negative electrodes 36, and the piezoelectric elements 32 has a bore extending through the center. The positive and negative electrodes 34 and 36 are electrically coupled to wires 38 and 40, respectively. The wires 38 and 40 are encased within a cable 42 and electrically connectable to the ultrasonic signal generator 12 of the ultrasonic system 10. An ultrasonic transducer drive module 600 with modulation may be located within the ultrasonic signal generator 12 or may be located within the handpiece assembly 60. The embodiments are not limited in this context.

The ultrasonic transducer 14 of the acoustic assembly 24 converts the electrical signal from the ultrasonic signal generator 12 into mechanical energy that results in primarily a standing acoustic wave of longitudinal vibratory motion of the ultrasonic transducer 24 and the blade 50 at ultrasonic frequencies. A suitable generator is available as model number GEN04, from Ethicon Endo-Surgery, Inc., Cincinnati, Ohio. When the acoustic assembly 24 is energized, a vibratory motion standing wave is generated through the acoustic assembly 24. The system is designed to operate at a resonance so that an acoustic standing wave pattern of amplitude is produced. The amplitude of the vibratory motion at any point along the acoustic assembly 24 depends on the location along the acoustic assembly 24 at which the vibratory motion is measured. A minimum or zero crossing in the vibratory motion standing wave is generally referred to as a node (i.e., where motion is minimal), and an absolute value maximum or peak in the standing wave is generally referred to as an anti-node (i.e., where motion is maximal). The distance between an anti-node and its nearest node is one-quarter wavelength ($\lambda/4$).

The wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to an activation element such as a foot switch 44 or other actuator to produce an acoustic standing wave in the acoustic assembly 24. The electrical signal causes disturbances in the piezoelectric elements 32 in the form of repeated small displacements resulting in large alternating compression and tension forces within the material. The repeated small displacements cause the piezoelectric elements 32 to expand and contract in a continuous manner along the axis of the voltage gradient to produce longitudinal waves of ultrasonic energy. The ultrasonic energy is transmitted through the acoustic assembly 24 to the blade 50 via an ultrasonic transmission waveguide 104.

In order for the acoustic assembly 24 to deliver energy to the blade 50, all components of the acoustic assembly 24 must be acoustically coupled to the blade 50. The distal end of the ultrasonic transducer 14 may be acoustically coupled at the surface 30 to the proximal end of the ultrasonic transmission waveguide 104 by a threaded connection such as a stud 48.

The components of the acoustic assembly 24 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24. It is also contemplated that the acoustic assembly 24 may incorporate any suitable arrangement of acoustic elements. The length of the ultrasonically actuatable blade 50 may be substantially equal to an integral multiple of one-half wavelengths ($n\lambda/2$).

A distal end 52 of the ultrasonic blade 50 may be disposed near an antinode in order to provide the maximum longitudinal excursion of the distal end. When the transducer assembly is energized, the distal end 52 of the ultrasonic blade 50 may be configured to move in the range of, for example, approximately 10 to 500 microns peak-to-peak, and preferably in the range of about 30 to 150 microns at a predetermined vibrational frequency of 55.5 kHz, for example.

The ultrasonic blade 50 may be coupled to the ultrasonic transmission waveguide 104. The ultrasonic blade 50 and the ultrasonic transmission waveguide 104 as illustrated are formed as a single unit construction from a material suitable for transmission of ultrasonic energy such as, for example, Ti6Al4V (an alloy of Titanium including Aluminum and Vanadium), Aluminum, Stainless Steel, or other known materials. Alternately, the ultrasonic blade 50 may be separable (and of differing composition) from the ultrasonic transmission waveguide 104, and coupled by, for example, a stud, weld, glue, quick connect, or other suitable known methods. The ultrasonic blade 50 may comprise a single-element (e.g., a scalpel or ball coagulator) or multiple-elements (e.g., a clamping coagulator). The length of the ultrasonic transmission waveguide 104 may be substantially equal to an integral number of one-half system wavelengths ($n\lambda/2$), for example. The ultrasonic transmission waveguide 104 may be preferably fabricated from a solid core shaft constructed out of material that propagates ultrasonic energy efficiently, such as titanium alloy (i.e., Ti6Al4V) or an aluminum alloy, for example.

The ultrasonic transmission waveguide 104 comprises a longitudinally projecting proximal end 54 to couple to the surface 30 of the ultrasonic transmission waveguide 104 by any suitable attachment means. In various embodiments, the proximal end 54 of the ultrasonic transmission waveguide 104 may be coupled to the surface 30 by a connection/union joint formed by a stud, weld, glue, quick connect, or other suitable known methods. In the embodiment illustrated in FIG. 1A, the proximal end of the proximal end 54 of the ultrasonic transmission waveguide 104 may be coupled to the surface 30 by a threaded connection such as the stud 48. The ultrasonic transmission waveguide 104 includes a plurality of stabilizing silicone rings or compliant supports 56 positioned at a plurality of nodes. The silicone rings 56 dampen undesirable vibration and isolate the ultrasonic energy from a removable sheath 58 assuring the flow of ultrasonic energy in a longitudinal direction to the distal end 52 of the blade 50 with maximum efficiency.

As shown in FIG. 1A, the outer sheath 58 protects the user and the patient from the ultrasonic vibrations of the ultrasonic transmission waveguide 104. The sheath 58 generally includes a hub 62 and an elongated tubular member 64. The tubular member 64 is attached to the hub 62 and has an opening extending longitudinally therethrough. The sheath 58 is threaded onto the distal end of the housing 16. The ultrasonic transmission waveguide 104 extends through the opening of the tubular member 64 and the silicone rings 56 isolate the ultrasonic transmission waveguide 104 from the outer sheath 58. The outer sheath 58 is attached to the ultrasonic transmission waveguide 104 with the isolator pin 112. The hole in the ultrasonic transmission waveguide 104 may be located nominally near a displacement node. The ultrasonic transmission waveguide 104 is threaded onto the handpiece assembly 60 by way of the stud 48. The flat portions formed on the hub 62 allow the hand piece assembly 60 to be torqued to a desired level.

The hub 62 of the sheath 58 is preferably constructed from plastic, and the tubular member 64 is fabricated from stainless steel. Alternatively, the ultrasonic transmission waveguide 104 may have polymeric material surrounding it to isolate it from outside contact.

In the embodiment illustrated in FIG. 1A, the distal end of the ultrasonic transmission waveguide 104 comprises the blade 50 formed as a single unitary piece. In other embodiments, the proximal end of the blade 50 may be detachably coupled to the distal end of the ultrasonic transmission waveguide 104 by an internal threaded connection, preferably at or near an antinode. In such embodiments, it is contemplated that the blade 50 may be attached to the ultrasonic transmission waveguide 104 by any suitable means, such as a welded joint or the like. The embodiments, however, are not limited in this context.

Figure 1B:
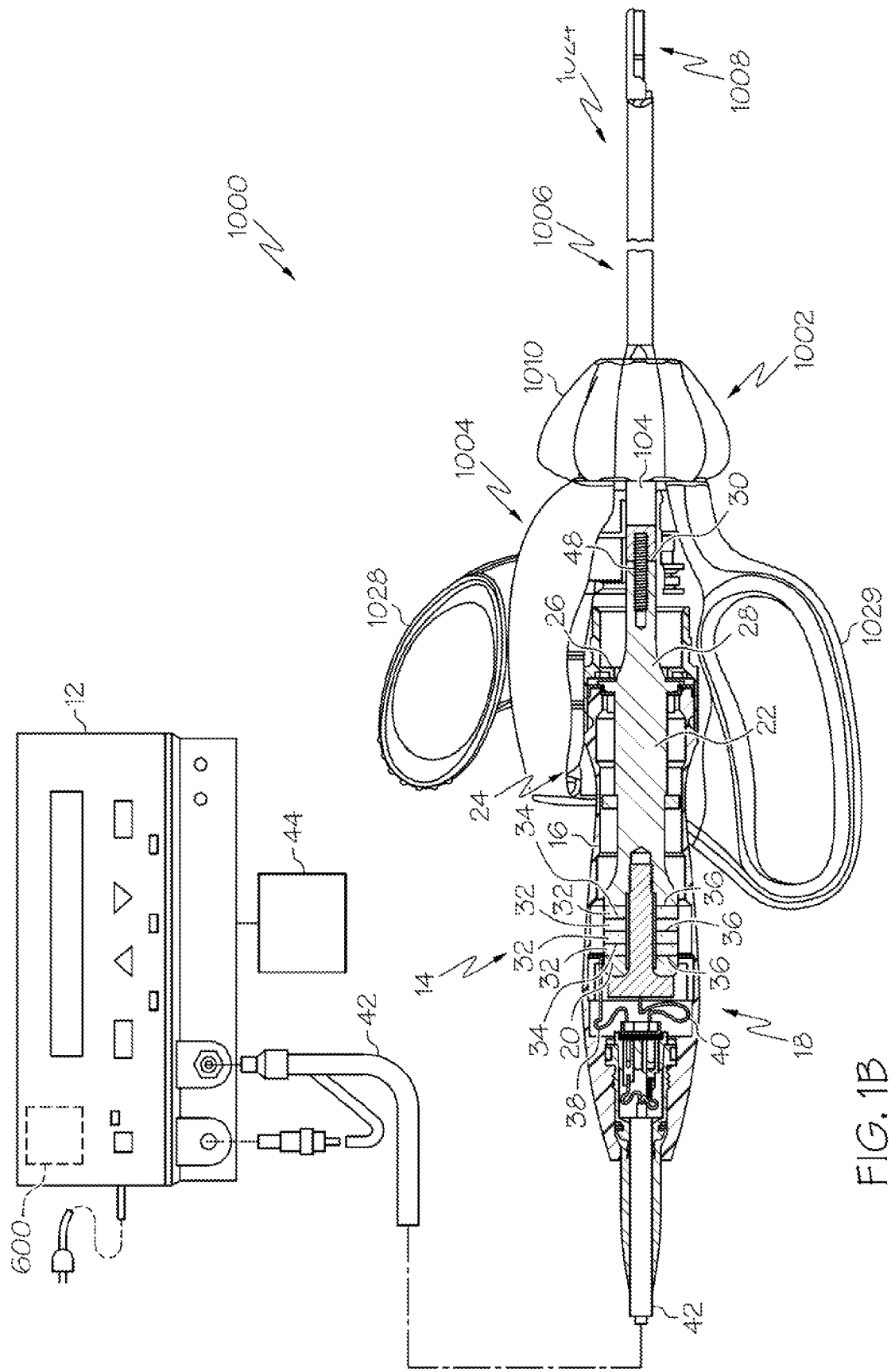
FIG. 1B illustrates one embodiment of an ultrasonic system comprising a multi-element end effector.

FIG. 1B illustrates one embodiment of an ultrasonic system 1000 comprising a multi-element end effector. One embodiment of the ultrasonic system 1000 comprises the ultrasonic generator 12 coupled to the ultrasonic transducer 14 described with reference to FIG. 1A. The ultrasonic transducer 14 is coupled to clamped coagulating shears 1002 comprising an instrument housing 1004. The acoustic assembly 18 delivers energy to the end effector 1016 (FIG. 3B) of the multi-element end assembly 1008 of the multi-element instrument. In order for the acoustic assembly 18 to deliver energy to the multi-element end effector or multi-element end assembly 1008, all components of the acoustic assembly 18 must be acoustically coupled to the ultrasonically active portions of the clamped coagulating shears 1002. Accordingly, the distal end of the ultrasonic transducer 14 may be acoustically coupled at the surface 30 to the proximal end of the ultrasonic transmission waveguide 104 by the threaded connection stud 48.

As previously discussed with reference to the ultrasonic system 10 shown in FIG. 1A, the components of the acoustic assembly 18 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 18. The acoustic assembly 18 may incorporate any suitable arrangement of acoustic elements.

Figure 2:
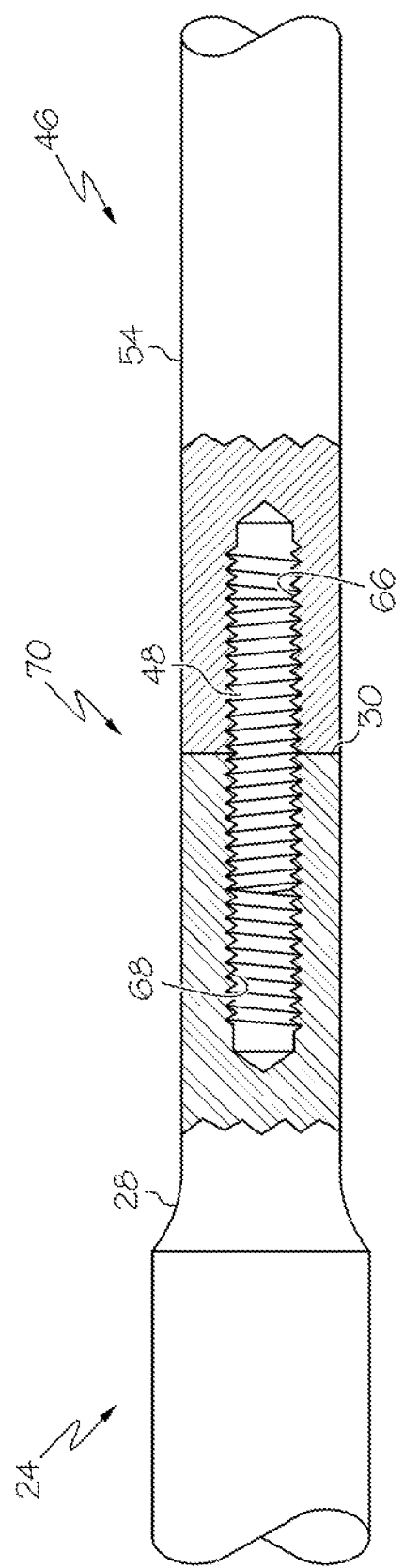
FIG. 2 illustrates one embodiment of a connection union/joint for an ultrasonic instrument.

FIG. 2 illustrates one embodiment of a connection union/joint 70 for an ultrasonic instrument. The connection union/joint 70 may be formed between the proximal end 54 of the ultrasonic transmission waveguide 104 and the surface 30 of the velocity transformer 28 at the distal end of the acoustic assembly 24. The proximal end of the proximal end 54 of the ultrasonic transmission waveguide 104 comprises a female threaded substantially cylindrical surface 66 to receive a portion of the threaded stud 48 therein. The distal end of the velocity transformer 28 also may comprise a female threaded substantially cylindrical surface 68 to receive a portion of the threaded stud 40. The surfaces 66, 68 are substantially circumferentially and longitudinally aligned.

Figure 3A:
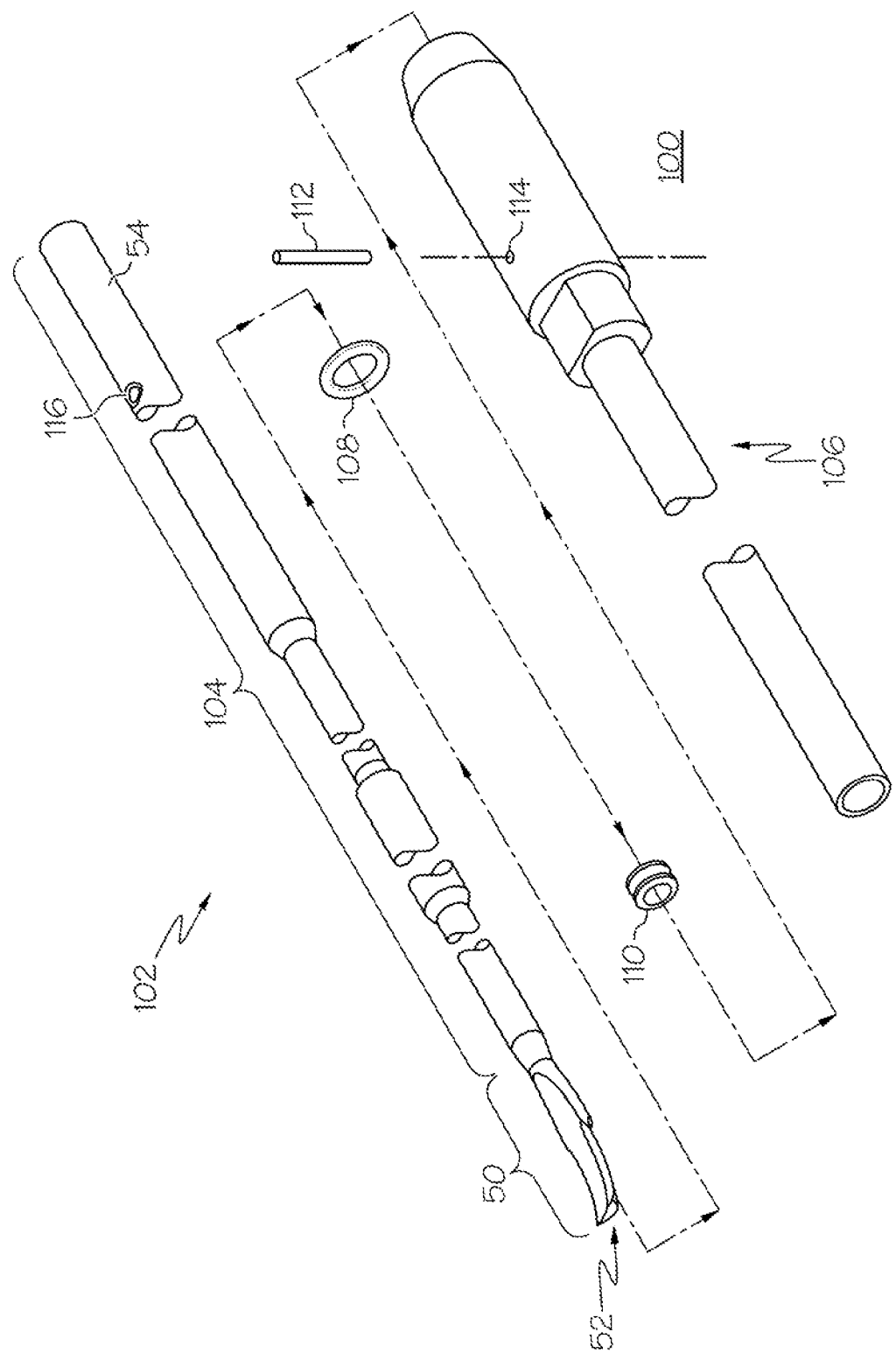
FIG. 3A illustrates an exploded perspective view of one embodiment of a single element end effector ultrasonic surgical instrument that may be coupled to the ultrasonic system illustrated in FIG. 1A.

FIG. 3A illustrates an exploded perspective view of one embodiment of a single element end effector ultrasonic surgical instrument 100. The ultrasonic surgical instrument 100 may be employed with the ultrasonic system 10 illustrated in FIG. 1A. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical blade embodiments disclosed herein should not be limited to use only in connection with the exemplary ultrasonic surgical instrument described above.

In the embodiment illustrated in FIG. 3A, the elongated transmission component is shown as the ultrasonic waveguide 104 and the end effector is shown as a single element end effector or blade 50 suitable to cut and/or coagulate tissue. The blade 50 may be symmetrical or asymmetrical.

The length of the blade 50 may be substantially equal to an integral multiple of one-half system wavelengths ($n\lambda/2$). The distal end 52 of the blade 50 may be disposed near an antinode in order to provide the maximum longitudinal excursion of the distal end 52. When the transducer assembly is energized, the distal end 52 of the blade 50 may be configured to move in the range of, for example, approximately 10 to 500 microns peak-to-peak, and preferably in the range of about 30 to 150 microns at a predetermined vibrational frequency.

The blade 50 may be coupled to the ultrasonic transmission waveguide 104. The blade 50 and the ultrasonic transmission guide 104 as illustrated are formed as a single unit of construction from a material suitable for transmission of ultrasonic energy such as, for example, Ti6Al4V (an alloy of titanium including aluminum and vanadium), aluminum, stainless steel, other known materials, or combinations thereof. Alternately, the blade 50 may be separable (and of differing composition) from the ultrasonic transmission waveguide 104, and coupled by, for example, a stud, weld, glue, quick connect, or other suitable known methods. The length of the ultrasonic transmission waveguide 104 may be substantially equal to an integral number of one-half system wavelengths ($n\lambda/2$), for example. The ultrasonic transmission waveguide 104 also may be preferably fabricated from a solid core shaft constructed out of material that propagates ultrasonic energy efficiently, such as titanium alloy (e.g., Ti6Al4V) or an aluminum alloy, for example. The ultrasonic transmission waveguide 104 also may be fabricated from a hollow core shaft constructed out of similar materials. The ultrasonic transmission waveguide 104 also may be fabricated with a combination solid/hollow core shaft, for example, a solid core shaft with hollow cavities positioned at various locations along the length of the shaft.

In the embodiment illustrated in FIG. 3A, the ultrasonic transmission waveguide 104 is positioned within the outer sheath 58 by a mounting O-ring 108 and a sealing ring 110. In other embodiments, one or more additional dampers or support members (not shown) also may be included along the ultrasonic transmission waveguide 104. The ultrasonic transmission waveguide 104 is affixed to the outer sheath 58 by the mounting pin 112 that passes through mounting holes 114 in the outer sheath 58 and a mounting hole 116 formed in the ultrasonic transmission waveguide 104.

FIG. 3B illustrates one embodiment of the clamped coagulating shears 1002 comprising a multi-element end effector as shown in FIG. 1B. FIG. 3C illustrates a perspective view of the multi-element end effector as shown in FIGS. 1B and 3B. With reference to FIGS. 1B, 3B and 3C, the clamped coagulating shears 1002 may be preferably attached to and removed from the acoustic assembly 18 as a unit. The proximal end of the clamped coagulating shears 1002 preferably acoustically couples to the distal surface 30 of the acoustic assembly 18. The clamped coagulating shears 1002 may be coupled to the acoustic assembly 18 by any suitable means.

The clamped coagulating shears 1002 preferably includes an instrument housing 1004 and an elongated member 1006. The elongated member 1006 may be selectively rotated with respect to the instrument housing 1004. The instrument housing 1004 includes a pivoting handle portion 1028 and a fixed handle portion 1029.

An indexing mechanism (not shown) is disposed within a cavity of the instrument housing 1004. The indexing mechanism is preferably coupled or attached on an inner tube 1014 to translate movement of the pivoting handle portion 1028 to linear motion of the inner tube 1014 to open and close the multi-element end assembly 1008. When the pivoting handle portion 1028 is moved toward the fixed handle portion 1029, the indexing mechanism slide the inner tube 1014 rearward to pivot the multi-element end assembly 1008 into a closed position. The movement of the pivoting handle portion 1028 in the opposite direction slides the indexing mechanism to displace the inner tube 1014 in the opposite direction, i.e., forwardly, and hence pivot the multi-element end assembly 1008 into its open position in the direction indicated by arrow 1020 as shown in FIG. 3B.

The pivoting handle portion 1028 includes a thumb loop 1030. A pivot pin 1032 is disposed through a first hole of the pivoting handle portion 1028 to allow pivoting as shown by arrow 1034 in FIG. 3B. As the thumb loop 1030 of the pivoting handle portion 1028 is moved in the direction of arrow 1034, away from the instrument housing 1004, the inner tube 1014 slides rearward to pivot the multi-element end assembly 1008 into a closed position.

The elongated member 1006 of the clamped coagulating shears 1002 extends from the instrument housing 1004. The elongated member 1006 preferably includes an outer member or outer tube 1012, an inner member or inner tube 1014, and a transmission component or ultrasonic transmission waveguide 104.

The multi-element end effector or multi-element end clamp arm assembly 1008 includes a clamp arm assembly 1018, a tissue pad 1036, and an ultrasonic blade 1016. The clamp arm assembly 1018 is pivotally mounted about a pivot pin (not shown) to rotate in the direction indicated by arrow 1038. The ultrasonic blade 1016 comprises a tapered concave surface 1040 extending inwardly into the blade body.

The ultrasonic surgical instrument 100 and the clamped coagulating shears 1002 may be sterilized by methods known in the art such as, for example, gamma radiation sterilization, Ethelyne Oxide processes, autoclaving, soaking in sterilization liquid, or other known processes. In the embodiment illustrated in FIGS. 1A and 3A, an ultrasonic transmission assembly 102 of the surgical instrument 100 includes the single element ultrasonically actuated end effector or blade 50 coupled to the ultrasonic transmission waveguide 104. The blade 50 and the ultrasonic transmission waveguide 104 are illustrated as a single unit construction from a material suitable for transmission of ultrasonic energy as previously discussed (e.g., Ti6Al4V, Aluminum, Stainless Steel, or other known materials). Alternately, the blade 50 may be separable (and of differing composition) from the ultrasonic transmission waveguide 104, and coupled by, for example, a stud, weld, glue, quick connect, or other known methods. In the embodiment illustrated in FIGS. 1B and 3B, the ultrasonic transmission assembly 1024 of the clamped coagulating shears 1002 includes the multi-element end assembly 1008 coupled to the ultrasonic transmission waveguide 104. The length of the ultrasonic transmission waveguide 104 may be substantially equal to an integral number of one-half system wavelengths ($n\lambda/2$), for example. The ultrasonic transmission waveguide 104 may be preferably fabricated from a solid core shaft constructed out of material that propagates ultrasonic energy efficiently, such as titanium alloy (i.e., Ti6Al4V) or an aluminum alloy, for example.

Figure 4A:
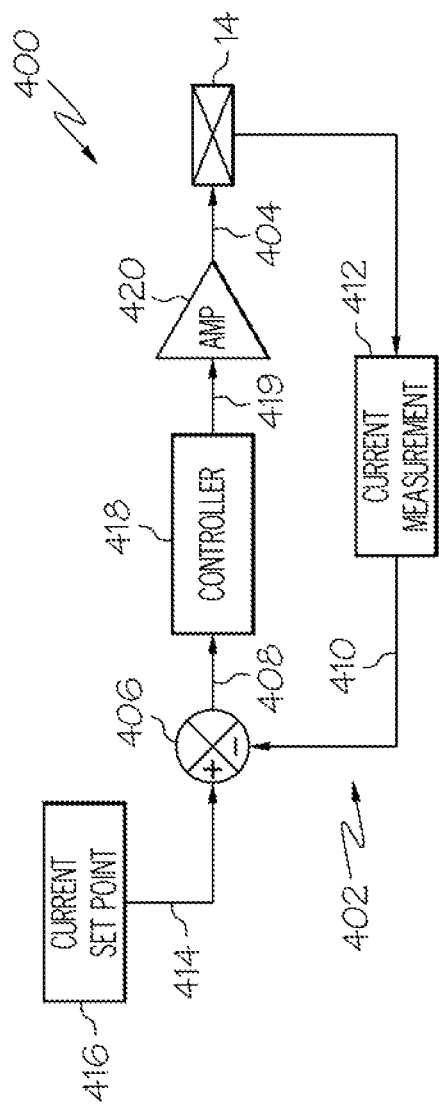
FIG. 4A illustrates one embodiment of an ultrasonic transducer drive module to driver the ultrasonic transducer.
Figure 4B:
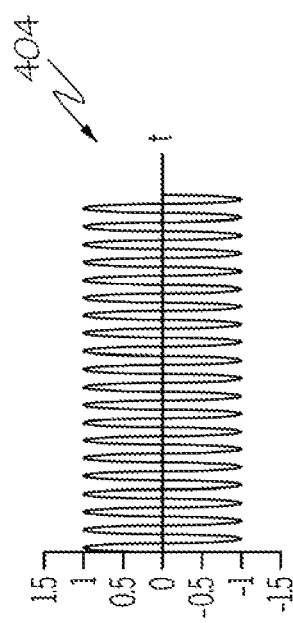
FIG. 4B illustrates the drive signal generated by one embodiment of the ultrasonic transducer drive module illustrated in FIG. 4A.

FIG. 4A illustrates one embodiment of an ultrasonic transducer drive module 400 to driver the ultrasonic transducer 14. The drive signal 404 generated by one embodiment of the ultrasonic transducer drive module 400 is illustrated in FIG. 4B. With reference to FIGS. 4A, B, the ultrasonic transducer drive module 400 may be a component of the ultrasonic signal generator 12. A current control loop 402 of the ultrasonic transducer drive module 400 controls the modulation of a drive signal 404, which is coupled to the transducer 14. The control loop 402 is a phase-locked loop (PLL) with current (i) and voltage (v) at 0° dropping into a resistive load, i.e., the transducer 14. The drive signal 404 varies the amplitude of the vibrations of the transducer 14 and consequently varies the longitudinal excursion of the distal end 52 of the blade 50. A summer module 406 in the current control loop 402 performs a summing function and generates an error signal 408 representative of the difference between the current 410 delivered to the transducer 14 as measured by the current measurement module 412 (e.g., root-mean-square or RMS) and a desired set point current 414 set by a current set point module 416. A controller 418 monitors the error signal 408 to increase or decrease the input voltage 419 to an amplifier 420. The amplifier 420 increases or decreases the voltage of the drive signal 404 so as to drive the error signal 408 to zero.

Without modulation, the drive signal 404 generated by the ultrasonic transducer drive module 400 has a substantially constant amplitude "A". The control loop 402 maintains the amplitude "A" of the drive current 410 constant current based on a selected power level from approximately 0 to 100% (e.g., GEN04, from Ethicon Endo-Surgery, Inc., Cincinnati, Ohio). Accordingly, the velocity of the distal end 52 of the blade 50 is maintained nearly constant even when the blade tip is "heavily loaded" with tissue, and thus the radiation pressure remains constant. Likewise the frequency "f" remains relatively constant even though there may be a slight decrease in frequency "f" as the distal end 52 of the blade 50 heats up. This means that size of the droplet particles 602 "d" also remains constant. Accordingly, the mist droplet particles experience substantially the same radiation and acoustic pressures and the same inertial and hydrodynamic drag forces.

Accordingly, the droplets move with the same motion and have a little opportunity to collide and coalesce.

Figure 5:
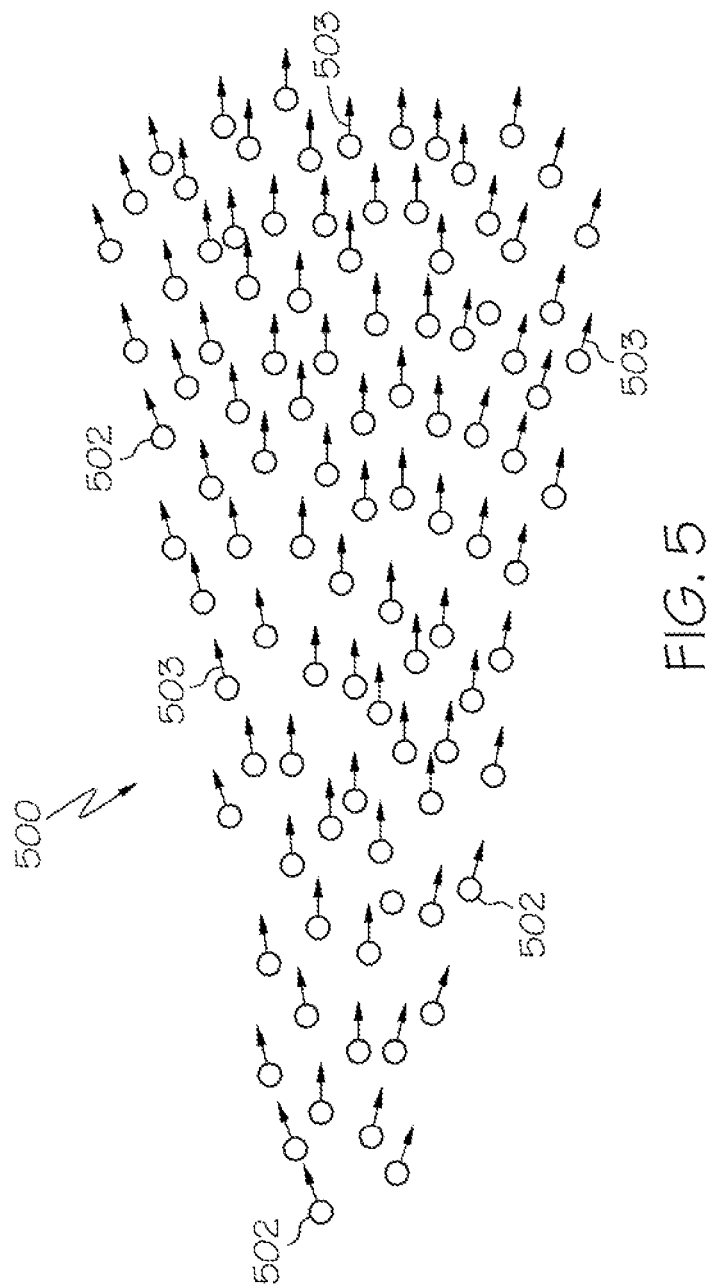
FIG. 5 illustrates a mist plume generated by an ultrasonically actuated end effector driven by a substantially constant amplitude "A" and constant frequency "f" drive signal.

FIG. 5 illustrates a mist plume 500 generated by an ultrasonically actuated end effector driven by a substantially constant amplitude "A" and constant frequency "f" drive signal. As previously discussed, when the distal end 52 of the blade 50 of the ultrasonic surgical instrument 100 is in contact with a fluid, a fine mist plume 500 emanates from the distal end 52 of the blade 50. The mist plume 500 is formed of individual relatively uniform droplet particles 502 moving at a substantially constant rate 503 of speed. The mist plume 500 limits the clarity of the view to the surgeon in the area of most interest. The mist plume 500 is generated when the ultrasonic blade 50 is activated to coagulate and transect tissue. Accordingly, the mist plume 500 is produced at that very site. The mist plume 500 may be reduced by decreasing the amplitude of the vibration at the distal end 52 of the blade 50. This, however, does not eliminate the mist plume 500 and higher amplitudes may be required in various applications. Accordingly, the elimination of the mist plume 500 remains an unmet need for the ultrasonic surgical end effectors 50.

When driven by a conventional ultrasonic drive signal, the ultrasonic blade 50 creates the mist plume 500 having a shape similar to that illustrated in FIG. 5. The shape of the mist plume 500 may be altered by altering the ultrasonic drive signal to achieve create agglomeration of the droplet particles 502 forming the mist plume 500. Agglomeration is the adherence of the droplet particle particles 502 into a small mass due to moisture, static charge or chemical or mechanical binding. Agglomeration of the droplet particles 502 is a process by which precipitation of the droplet particles 502 occurs by the collision or contact of smaller droplet particles 502 to coalesce into larger heavier particles. Work performed in the past (circa 1950's) has shown the technical feasibility to defog runways at airports by an agglomeration process using ultrasonic energy. The actual implementation if such large scale system may have been precluded by the large power requirements and the number and size of ultrasonic sirens necessary for implementation of the process. In accordance with the principles of particle agglomeration, the ultrasonic transducer drive module 400 may be configured to produce ultrasonic energy to mitigate the mist plume 500 emanating from the distal end 52 of the ultrasonic blade 50.

The distal end 52 of the ultrasonic blade 50 produces radiation pressure when it is activated with the ultrasonic signal generator 12. Radiation pressure is a hydrostatic pressure created by the ultrasonic vibrations in gases and liquids due to material nonlinearities. This radiation pressure in an ideal gas depends on the average energy in the medium, which may be denoted as $\langle E \rangle$. The average energy $\langle E \rangle$ is proportional to the square of the velocity in the distal medium. The relations for radiation pressure $P_r$ and $\langle E \rangle$ may be expressed formulaically in equations (1), (2), and (3) as follows:

$$P_r = \frac{\gamma+1}{4} \cdot \langle E \rangle \tag{1}$$

$$\langle E \rangle = \frac{1}{2} \cdot \rho_o v^2 \tag{2}$$

$$v = \omega \cdot d \tag{3}$$

The size of the droplet particles 502 forming the mist plume 500 may be defined in accordance with the following physical behavior model. Although the physics underlying the generation of mist (i.e., the atomization of liquids) is fairly complex, in most regimes, the average diameter "d" of the fluid droplets may be defined formulaically in accordance with equation (4):

$$d = 0.34 \left( \frac{8\pi \cdot T}{\rho_o \cdot f^2} \right)^{\frac{1}{3}} \tag{4}$$

Where T is the surface tension and $\rho_o$ is the density of the fluid (or liquid) and "f" is the frequency of vibration. In accordance with equation (4), droplet particle size "d" is inversely proportional to frequency "f" raised to the ⅔ power. This means that as the frequency "f" increases, the droplet particle 502 size "d" decreases. There exists a distribution of droplets size about the average size given by equation (4) above. The distribution, however, is a relatively tight distribution, so the droplet particle 502 size "d" in the distribution is nearly uniform.

The size of the droplet particles 502 in the mist plume 500 are distributed over a substantial range and potentially stratified. When the mist plume 500 is insonified by a field generated by a vibrational source, such as the ultrasonically driven blade 50, different sized droplet particles respond differently to the vibrational field. The droplet particles 502 move at different rates and in different directions due to their position in the vibrational field and their size in terms of the inertial and hydrodynamic drag forces causing the droplet particles 502 to collide and potentially coalesce. At some level, the increased size of the droplet particle 502 is sufficient to enable the larger heavier droplet particle to "drop out" because of increased gravitational force.

Figure 6A:
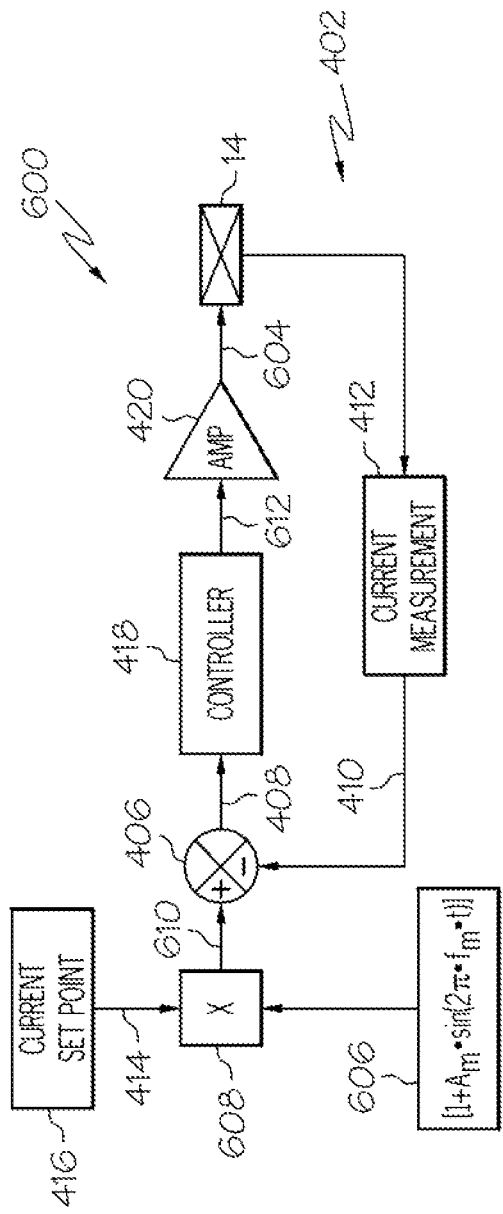
FIG. 6A illustrates one embodiment of an ultrasonic transducer drive module with modulation.
Figure 6B:
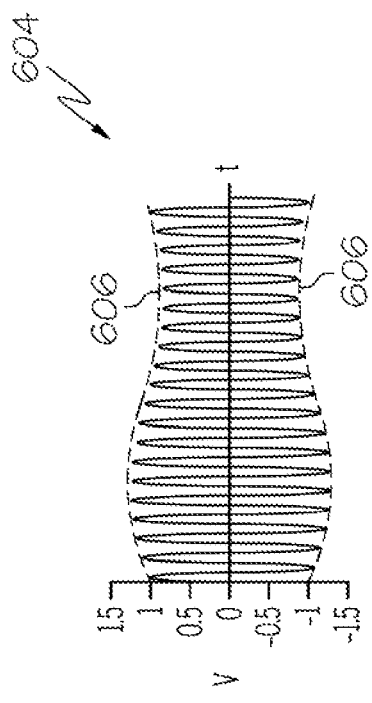
FIG. 6B illustrates the modulated drive signal generated by one embodiment of the ultrasonic transducer drive module illustrated in FIG. 6A.

FIG. 6A illustrates one embodiment of the ultrasonic transducer drive module 600 with modulation. A modulated drive signal 604 generated by one embodiment of the ultrasonic transducer drive module 600 is illustrated in FIG. 6B. With reference to FIGS. 6A, B, the ultrasonic transducer drive module 600 may be a component of one embodiment of the ultrasonic signal generator 12. The current control loop 402 of the ultrasonic transducer drive module 600 controls the modulation of the drive signal 604, which is coupled to the transducer 14. The ultrasonic transducer drive module 600 generates the drive signal 604 and delivers a total "RMS" current 410 to the transducer 14. As the load increases, the current control loop 402 increases the drive signal 604 voltage. The drive signal 604 driving the transducer 14 remains a sinusoid with an amplitude "A", and the current control loop 402 maintains the RMS current equal to the current set point signal 414 set by the set point module 416.

A modulation waveform 606 (also shown in FIG. 6B in phantom line superimposed on the modulated drive signal 604) is modulated onto the current set point signal 414 by a modulator 608. The modulation waveform 606 "$S_m$" may be expressed as:

$$S_m = 1 + A_m \cdot \sin(2\pi \cdot f_m \cdot t) \tag{5}$$

The modulation waveform 606 "$S_m$" comprises a modulation amplitude component "$A_m$" and a modulation frequency component "$f_m$". In the embodiment illustrated in FIG. 6A, the sinusoidal drive signal 604 driving the transducer 14 is a varying amplitude sine wave signal. A slowly varying amplitude component is impressed onto the sinusoidal drive signal 604 by the modulator 608. The modulated signal 610 from the modulator 608 is provided to one input of the summer module 406. The control loop 402 forces the RMS current to be equal to the modulated signal 610, which is formed of the set point current 414 component and the modulation waveform 606 component. The frequency response of the control loop 402 may be selected to track changes in the load (e.g., the transducer 14) and should be greater than the modulation frequency "$f_m$".

The modulation waveform 606 applied to the drive signal 604 will modulate the vibrations of the transducer 14 and hence the longitudinal excursions of the blade 50. The shape of the modulation waveform 606 influences the relative motions of droplet particles 502 forming the mist plume 500 emanating from the distal end 52 of the blade 50. The modulation waveform 606 applied to the drive signal 604 may take the form of a slowly-varying alternating current (AC) signal to slowly vary the set point current 414 applied by the current set point module 416. The frequency of the modulation waveform 606 may be selected such that it is much less than the resonant frequency "f" of the ultrasonic transducer 14 and slower than the time constant associated of the current control loop 402. With respect to the control loop 402, the modulation waveform 606 should develop as a varying set-point signal generated by the current set point module 416 and not as an error signal that requires correction. In one embodiment, the modulation waveform 606 may take the form of a sinusoidal signal. In other embodiments, however, the modulation waveform 606 may take the form of a saw tooth wave or square wave or any suitable waveform shape.

The shape of the modulation waveform 606 affects the relative motions between the droplet particles 502 forming the mist plume 500, which is generated by the constant amplitude "A" and constant frequency "f" drive signal 404 without modulation. The droplet particles 502 are substantially uniform in size when no modulation waveform is applied to the drive signal 404. The droplet particles 502 are substantially uniform in size because they emanate from the distal end 52 of the blade 50 at essentially the same radiation pressure and, accordingly, at the same relative rate or motion. Modulation waveforms with high crest factors may produce different and more significant results in the relative motion of the droplet particles 502 of the mist plume 500. A trade off exists, however, because different types of modulation waveforms may have higher frequency components that may interfere with the operation of the control loop 402.

Figure 7:
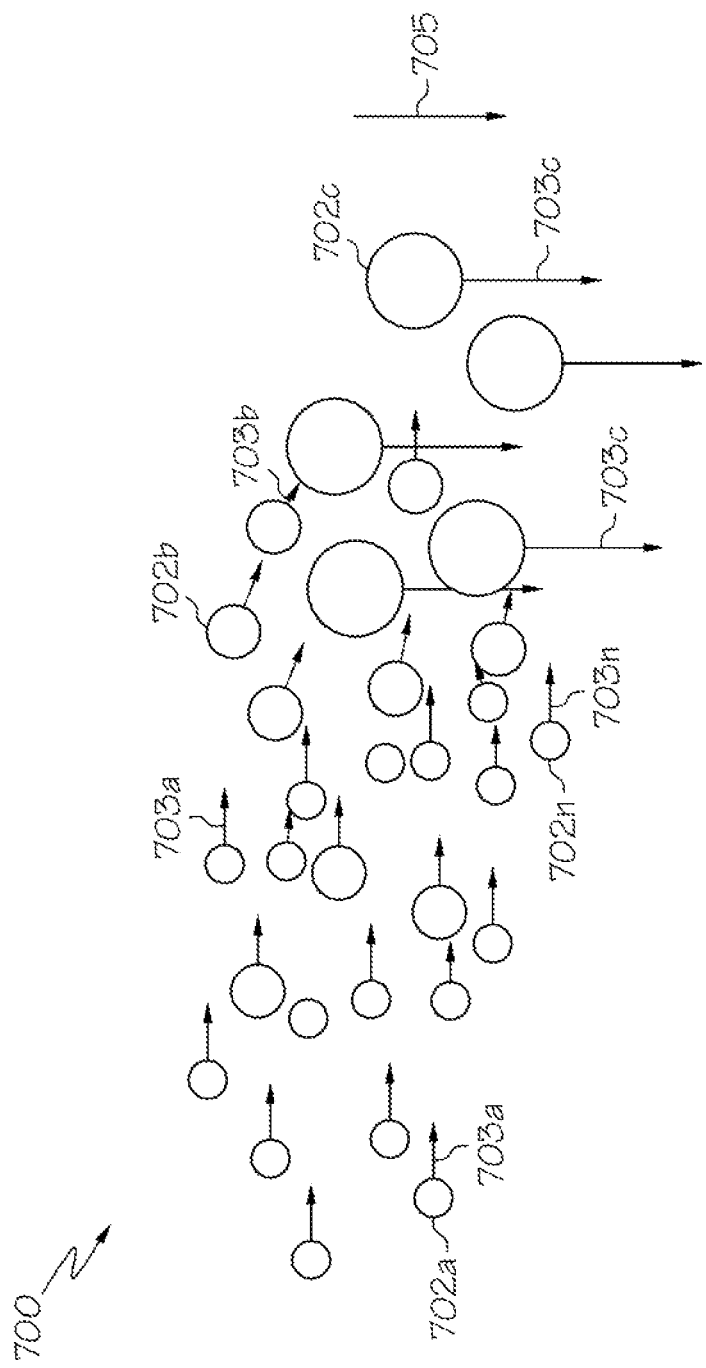
FIG. 7 illustrates a mist plume emanating from a distal end of an end effector driven by a modulated drive signal generated by one embodiment of the ultrasonic transducer drive module with modulation illustrated in FIG. 6A.

FIG. 7 illustrates a mist plume 70 emanating from the distal end 52 of the blade 50 driven by the modulated drive signal 604 generated by one embodiment of the ultrasonic transducer drive module 600 with modulation illustrated in FIG. 6A. The mist plume 700 illustrates the effect that the modulation drive signal 404, 604 imparts on the distal end 52 of the blade 50 has on the droplet particles $702_{a-n}$, where n is an integer that represents the total number of droplet particles in the mist plume 700. As illustrated for convenience and clarity, the size of the droplet particles $702_{a-n}$ varies and are not substantially uniform in size like the droplet particles 502 forming the mist plume 500 (FIG. 5) with no modulation. The droplet particles $702_{a-n}$ are now less uniform in size because they are being pushed out by the radiation pressure at different rates indicated as $703_{a-n}$, due to the modulation effects of the drive signal 604. Accordingly, with modulation applied to the drive signals 404, 604, the droplet particles $702_{a-n}$ have a non-uniform motion that enables individual droplet particles $702_{a-n}$ to collide and coalesce, thus forming larger droplet particles $702_b$ and $702_c$ moving at different respective rates $703_b$ and $703_c$. As the droplet particles $702_{a-n}$ grow in size, gravitational force dominates, and the larger droplet particles $702_c$ fall out of the mist plume 700 under the influence of gravity 705.

Reducing the radiation force may in large part account for "reduced" mist generation. For example, for an ultrasonic instrument, which operates at a 70% lower amplitude as compared with other ultrasonic instruments, the radiation pressure is nearly one half that of the other ultrasonic instruments. The lower radiation pressure pushes out the fluid droplets with half the force. Therefore the mist plume would be of substantially lesser volume. The droplet particle 502 size "d" produced by such system should be the same for all end effectors 50 (e.g., blades) because the frequency "f" is fixed by design at a nominal 55.5 kHz and only decreases slightly as the blade 50 (e.g., blade) heats up.

In one embodiment, the ultrasonic transducer drive module 600 modifies the drive signal 604 to mitigate the mist plume 500 (FIG. 5) and generate the mist plume 700 (FIG. 7) by modulating the drive signal 604 with the modulation waveform 606. This may comprise modulating either the current drive signal 604 to change the amplitude "A" of the drive signal 604, the frequency "f" of the drive signal 604, or any combination thereof. In one embodiment, the ultrasonic transducer drive module 600 varies the radiation pressure at the distal end 52 of the blade 50 so that the droplet particles $702_{a-n}$ at different distances from the distal end 52 move out from the distal end 52 at different relative rates. The relative motion between the droplet particles $702_{a-n}$ creates greater opportunities for collision and coalescence. As more droplet particles $702_{a-n}$ coalesce, the range of droplet particle 502 sizes expands creating more collisions and larger droplets, e.g., $702_b$ and $702_c$. At some droplet particle $702_c$ size, gravitational force dominates to cause the large droplet particles $702_c$ to drop out of the mist plume.

In one embodiment, the ultrasonic transducer drive module 600 also may be employed to vary the size of the droplet particles $702_{a-n}$, produced by the distal end 52 of the blade 50. Accordingly, in one embodiment, the size of the droplet particles $702_{a-n}$ is dependent on the modulation frequency "$f_m$" only (for a given liquid) and not on the amplitude "A". Accordingly, the size of the droplet particles 502 may vary in accordance with the modulation frequency "$f_m$". Given that the ultrasonic surgical instrument 100 is a high "Q" device, the modulation frequency "$f_m$" may be varied only a few hertz. It may be possible to intentionally drive the system at another resonance for a brief period of time at a low duty cycle. This technique, however, may be impractical and may lead to other undesirable effects. Nevertheless, this feature may be incorporated in other embodiments and should be considered part of the scope of the claims attached hereto.

Figure 8:
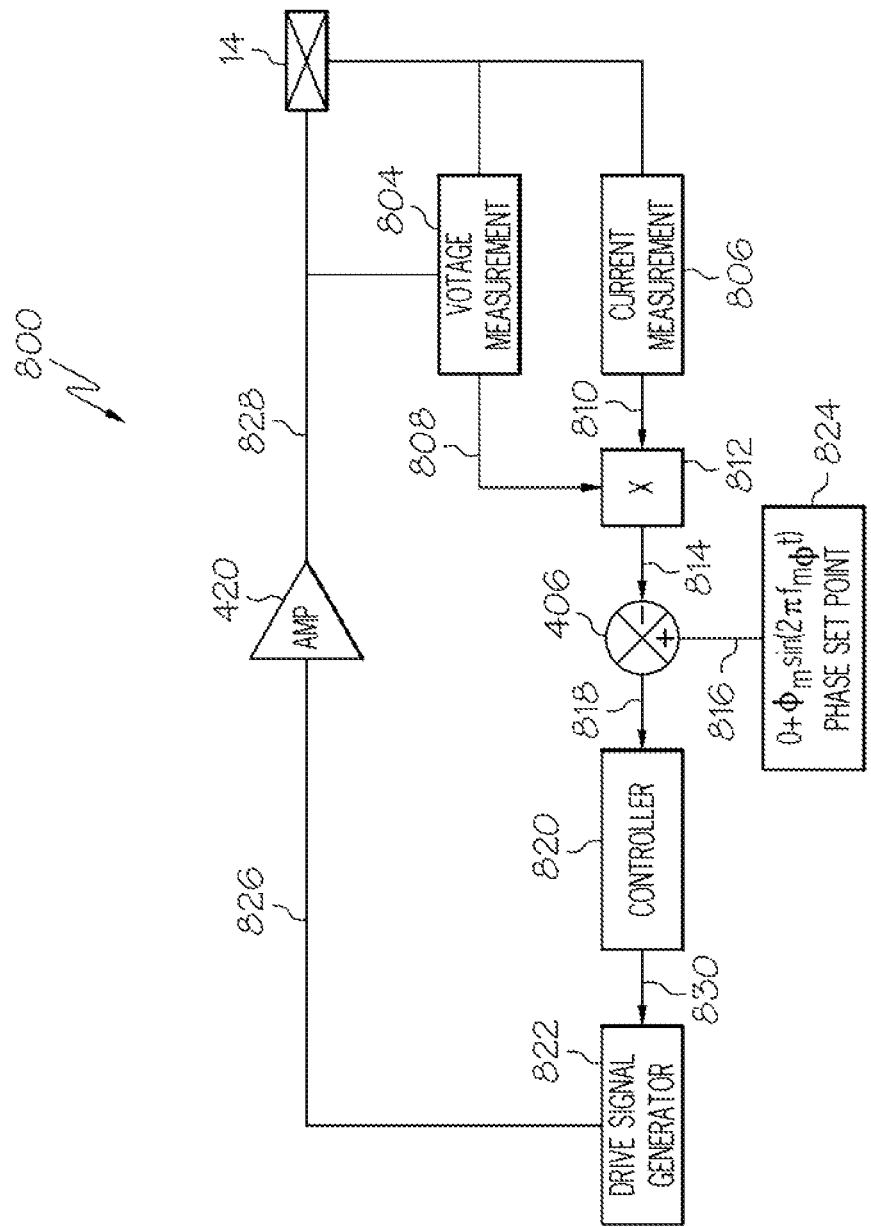
FIG. 8 illustrates one embodiment of an ultrasonic transducer drive module with phase modulation.

FIG. 8 illustrates one embodiment of an ultrasonic transducer drive module 800 with phase modulation. A phase modulated drive signal 828 is employed to drive the transducer 14. The module 800 may be a component of one embodiment of the ultrasonic signal generator 12. A voltage measurement module 804 measures the voltage across the transducer 14 and provides a voltage measurement signal 808 with a phase $\phi_v$ to a phase detector 812. A current measurement module 806 measures the current through the transducer 14 and provides a current measurement signal 810 with a phase $\phi_i$ to the phase detector 812. The phase detector 812 determines the phase difference between the voltage measurement signal 808 and the current measurement signal 810 and provides a relative phase signal 814 proportional to the phase difference. The relative phase signal 814 nominally varies about zero because the transducer 14 is generally driven with real power. A phase set point module 824 generates a phase modulation waveform 816 "$S_m$" that varies the phase of a modulation drive signal 828 about the nominal set point, typically zero phase. The phase modulation waveform 816 and the relative phase signal 814 are fed to inputs of the summer module 406. The summer module 406 performs a summing function and generates an error signal 818 proportional to the difference between the phase modulation waveform 816 and the relative phase signal 814. A controller 820 monitors the error signal 818 and provides a frequency control signal 830 to a signal generator 822. The signal generator 822 generates a sinusoidal drive signal 826 having a nominal frequency. The frequency control signal 830 adjusts the frequency of the sinusoidal drive signal 826 proportionally to the error signal 818. The sinusoidal drive signal 826 is amplified by a power amplifier 420 to produce a phase modulation drive signal 828 to drive the transducer 14.

In digital implementations, rather than determining the relative phase differences between the various signals, the modules determine the relative differences in timing between various digital signals in accordance with well established digital signal processing techniques. For example, when the voltage measurement module 804 and the current measurement module 806 are implemented in with digital modules, the phase detector 812 may be replaced by suitable digital circuit module to determine the relative time delay or time difference between each signal component. Likewise, instead of generating the frequency control signal 830, in the digital domain the controller 820 adjusts the clock or timing of the drive signal generator 822.

The phase modulation waveform 816 "$S_{m\phi}$" may be expressed as:

$$S_{m\phi}=0+\phi_m \cdot \sin(2\pi \cdot f_{m\phi} \cdot t) \quad (6)$$

The phase modulation waveform 816 "$S_{m\phi}$" comprises a modulation phase component "$\phi_m$" and a modulation frequency component "$f_{m\phi}$". As previously discussed, the phase modulation waveform 816 "$S_{m\phi}$" varies about "0" because the transducer 14 is generally driven with real power, therefore, nominally there is no phase difference between the voltage measurement signal 808 and the current measurement signal 810 other than the variation in phase (or frequency) injected by the phase set point module 824. In the embodiment illustrated in FIG. 8, the sinusoidal drive signal 826 is amplified by the power amplifier 420 to produce the drive signal 828 with a varying phase or frequency of the phase modulation waveform 816. In this manner, a slowly varying phase or frequency component is impressed onto the sinusoidal drive signal 828. Under relatively light tissue loads, the frequency variation may be in the order a few hertz. Under relatively heavy tissue loads, the frequency variation may be in the order of tens of hertz because of the lower Q. The phase or frequency changes are relatively small. In accordance with equation (4), droplet particle size "d" is inversely proportional to frequency "f" raised to the ⅔ power (e.g., $f^{2/3}$). Accordingly, as the frequency "f" increases, the droplet particle size "d" decreases. There exists a distribution of droplets size about the average size given by equation (4) above. The distribution, however, is a relatively tight distribution, so the droplet particle size "d" in the distribution is nearly uniform. Due to the variations in phase or frequency injected into the sinusoidal drive signal 826, the ultrasonic blade 50 driven by the phase modulation drive signal 828 acts on the fluid droplets to produce non-uniform particle sizes as shown in the mist plume 700 (FIG. 7). The non-uniform particle size helps the fluid droplet particles $702_{a-n}$, to coalesce and drop out of the mist plume 700 under the influence of gravity 705.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. In addition, combinations of the described embodiments may be used. For example, the end effector may be adapted with a concave blade tip coated with a "hemophobic" material. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method, comprising:
receiving a modulation waveform comprising a modulation amplitude ($A_m$) component and a modulation frequency ($f_m$) component; wherein the modulation waveform is defined by the following relationship:

$$S_m = 1 + A_m \cdot \sin(2\pi \cdot f_m \cdot t);$$

generating a modulated drive signal with a drive module; and coupling the modulated drive signal to a transducer, wherein the transducer is coupled to an end effector having a distal end;

wherein the distal end is movable in response to vibrations produced by the transducer in response to the modulated drive signal.

2. The method of claim 1, comprising:

receiving a current set point signal at a first input of a modulator;

receiving the modulation waveform at a second input of the modulator;

generating a modulation signal by modulating the current set point signal with the modulation waveform; and coupling the modulation signal with a current control loop to control the modulated drive signal coupled to the transducer.

3. The method of claim 2, wherein receiving the modulation waveform comprises receiving a time varying modulation amplitude ($A_m$) component.

4. The method of claim 2, wherein receiving the modulation waveform comprises receiving a time varying modulation frequency ($f_m$) component.

5. The method of claim 2, wherein receiving the modulation waveform comprises receiving a time varying modulation amplitude ($A_m$) component and a time varying modulation frequency ($f_m$) component.

6. The method of claim 1, comprising:

imparting a radiation pressure proportional to the modulated drive signal onto a fluid droplet particle in contact with the distal end of the end effector in response to the modulated drive signal.

\* \* \* \* \*